US006581437B2

(12) United States Patent
Chrystall et al.

(10) Patent No.: US 6,581,437 B2
(45) Date of Patent: Jun. 24, 2003

(54) MOTION PLATFORM AND METHOD OF USE

(75) Inventors: Keith G. Chrystall, Calgary (CA); Simon P. Monckton, Calgary (CA); Mark Oleson, Winnipeg (CA)

(73) Assignee: Alberta Research Council Inc., Edmonton (CA)

( * ) Notice: Subject to any disclaimer, the term of this patent is extended or adjusted under 35 U.S.C. 154(b) by 82 days.

(21) Appl. No.: 09/853,657

(22) Filed: May 14, 2001

(65) Prior Publication Data

US 2002/0029610 A1 Mar. 14, 2002

(51) Int. Cl.[7] .................................................. G01N 3/56
(52) U.S. Cl. ............................................. 73/7; 73/865.6
(58) Field of Search ........................ 73/7, 865.6, 379.1, 73/379.4

(56) References Cited

U.S. PATENT DOCUMENTS

| | | |
|---|---|---|
| 4,130,007 A | 12/1978 | Hayashi |
| 4,327,572 A | 5/1982 | Pitman et al. |
| 4,432,223 A | 2/1984 | Paquette et al. |
| 5,305,981 A | 4/1994 | Cunningham et al. |
| 5,401,128 A | 3/1995 | Lindem et al. |
| 5,656,905 A | 8/1997 | Tsai |
| 5,901,936 A | 5/1999 | Bieg |
| 5,909,939 A | 6/1999 | Fugmann |
| 5,916,328 A | 6/1999 | Pritschow |
| 5,931,098 A | 8/1999 | Bates |
| 5,980,256 A | 11/1999 | Carmein |
| 5,987,726 A | 11/1999 | Akeel |
| 6,007,631 A | 12/1999 | Prentice et al. |
| 6,024,526 A | 2/2000 | Slocum et al. |
| 6,041,500 A | 3/2000 | Terpstra |
| 6,047,610 A | 4/2000 | Stocco et al. |
| 6,162,189 A * | 12/2000 | Girone et al. ............... 600/592 |
| 6,289,743 B1 * | 9/2001 | Norton ........................ 73/847 |

OTHER PUBLICATIONS

Goldsmith, Peter; "Design of a Robot for Sport Shoe Testing", Paper presented at ICARCV '98 International Conference Control, Auto, Robotics & Vision) Singapore Dec. 1998.
Girone, Michael, J., et al. "The 'Rutgers Ankle' Orthopedic Rehabilitation Interface" Proceedings of the ASME Hoptics Symposium; Dse. vol. 57 p.305–372—Nov. 1999.
Badaliance, R. et al. Effects of Computational Technology on Composite Materials Research: The Case of Dissipated Energy Density, First Hellenic Conference on Composite Materials Research, Jul. 2–5, Democritus University of Thrace, Xanthi, Greece.
Six Dimensional Loader, Search of NRL Materials Science and Technology Division, Code 630 Naval Research Laboratory, Washington, D.C. 20375 Website.
LME Hexapod Machine, Search of LME Website.
Hexapod, Search of Polytec PI Home Page.
M–850 Hexapod 6–Axis Parallel Kinematics Robot, Search of Physikinstruments.com website.
Characterization, Remote Access, and Simulation of Hexapod Machines, Search of National Advanced Manufacturing Testbed Website.

* cited by examiner

Primary Examiner—Daniel S. Larkin
Assistant Examiner—Nashmiya Fayyaz
(74) Attorney, Agent, or Firm—Bennett Jones LLP (57) ABSTRACT

A novel Stewart platform includes electromagnetic linear actuators. The motion platform may be included in an apparatus and method for testing footwear where a stationary shoe is struck by the motion platform.

12 Claims, 11 Drawing Sheets

MOTION PLATFORM AND METHOD OF USE

FIELD OF THE INVENTION

The present invention relates to a motion platform and in particular, to a method and apparatus incorporating a motion platform to test shoes.

BACKGROUND OF THE INVENTION

Motion platforms are devices that can move an object through an arbitrary trajectory in 3 dimensional space within a given working volume while maintaining precise control over the position, velocity and acceleration of the object. One type of mechanism that is suitable for creating a general-purpose motion platform is a Stewart platform or hexapod. Stewart platforms are well-known and include a parallel linkage that permits movement with 6 degrees of freedom: independent and simultaneous translation and rotation about and along each of the three primary Cartesian axes X, Y and Z. A Stewart platform includes six "legs" each of which is extendible to translate and rotate a platform about all three Cartesian axes. In general, Stewart platforms are known for their low mass, high mechanical stiffness and large payload capacities.

Typically, Stewart platforms have extendible "legs" which are hydraulic, pneumatic, lead screw electric or ball screw electric actuators and are used in automated assembly lines. Examples of automatic assembly machines using a Stewart platform are disclosed in U.S. Pat. Nos. 6,041,500 and 5,987,726. These prior art Stewart platforms generate tremendous thrust, particularly hydraulically actuated platforms, at the expense of velocity and are limited to accuracy in the range of one to two millimeters.

In many applications, it is desirable to generate platform velocities of greater than 2.5 meters per second and up to 3 m/s or more, with accuracy in the sub-millimeters range and maintain thrust in the range of 1000 pounds. Further it would be desirable if such a platform could also deliver vertical acceleration in excess of 3 g and rotation rates of up to 1000 degrees per second. One such application is footwear testing.

It is desirable to determine the effect of shoe design on foot motion and impact control, particularly for athletic footwear. Athletic footwear manufacturers typically evaluate human subjects wearing test shoes during prescribed movements. These human tests are time-consuming, unreliable and fail to reveal internal motion or forces within the ankle or leg, apart from subjective observations by the test subject, which are inherently unreliable.

Robotic footwear testers have been directed at simulating walking or running motions. One example is the tester disclosed in U.S. Pat. No. 4,130,007. The difficulty with such robotic testers is that they are mechanically complex yet only very simple walking or running motions may be simulated and they cannot accurately simulate complex motions. As a result, only very limited test information is obtained.

Therefore, there is a need in the art for methods and apparatuses to robotically test footwear which may incorporate a novel motion platform.

SUMMARY OF THE INVENTION

The present invention is directed to a novel motion platform falling within the generic category of Stewart platforms or hexapods. In particular, the motion platform of the present invention is incorporated into a novel apparatus and method for testing footwear.

Therefore, in one aspect, the invention comprises a motion platform comprising a base, a platform, a motion controller and at least 6 linear actuating mechanisms disposed between and connected to the base and the platform, wherein each actuating mechanism comprises an electromagnetic linear actuator comprising an electric thrust block and a magnetic thrust rod and each actuating mechanism is controlled by the motion controller.

In another aspect, the invention may comprise a shoe testing apparatus comprising:

(a) a fixed artificial foot including a force sensor, for wearing the shoe;

(b) a motion platform capable of moving and being controlled with 6 degrees of freedom;

(c) means for actuating the motion platform and striking the shoe with the platform in a manner simulating the running or walking gait of a shoe wearer;

(d) means for recording the forces sensed and transmitted by the force sensor.

In another aspect, the invention may comprise a method of testing a shoe, comprising the steps of:

(a) fitting an artificial foot within the shoe, providing a force sensor attached to the artificial foot and fixing the foot and shoe in position;

(b) providing a motion platform capable of moving and being controlled in 6 degrees of freedom;

(c) providing a foot trajectory and transforming the foot trajectory to a platform trajectory;

(d) actuating the motion platform with the platform trajectory to strike the shoe; and (e) recording the resulting forces with the force sensor.

BRIEF DESCRIPTION OF THE DRAWINGS

The invention will now be described by way of an exemplary embodiment with reference to the accompanying simplified, diagrammatic, not-to-scale drawings. In the drawings.

DETAILED DESCRIPTION OF THE INVENTION

The present invention provides for a motion platform and a method of using a motion platform to test footwear. When describing the present invention, the following terms have the following meanings, unless indicated otherwise. All terms not defined herein have their common art-recognized meanings.

The term "Stewart platform" or "hexapod" refers to an octahedral platform including stiff extendible legs actuating a platform in all six degrees of freedom: translation and rotation about three Cartesian axes. Each leg is attached to a base and the platform by flexible joints.

The term "comprises" or "comprising" or "includes" or "including" shall mean "includes without limitation" or "including without limitation" as the case may be.

Figure 1:
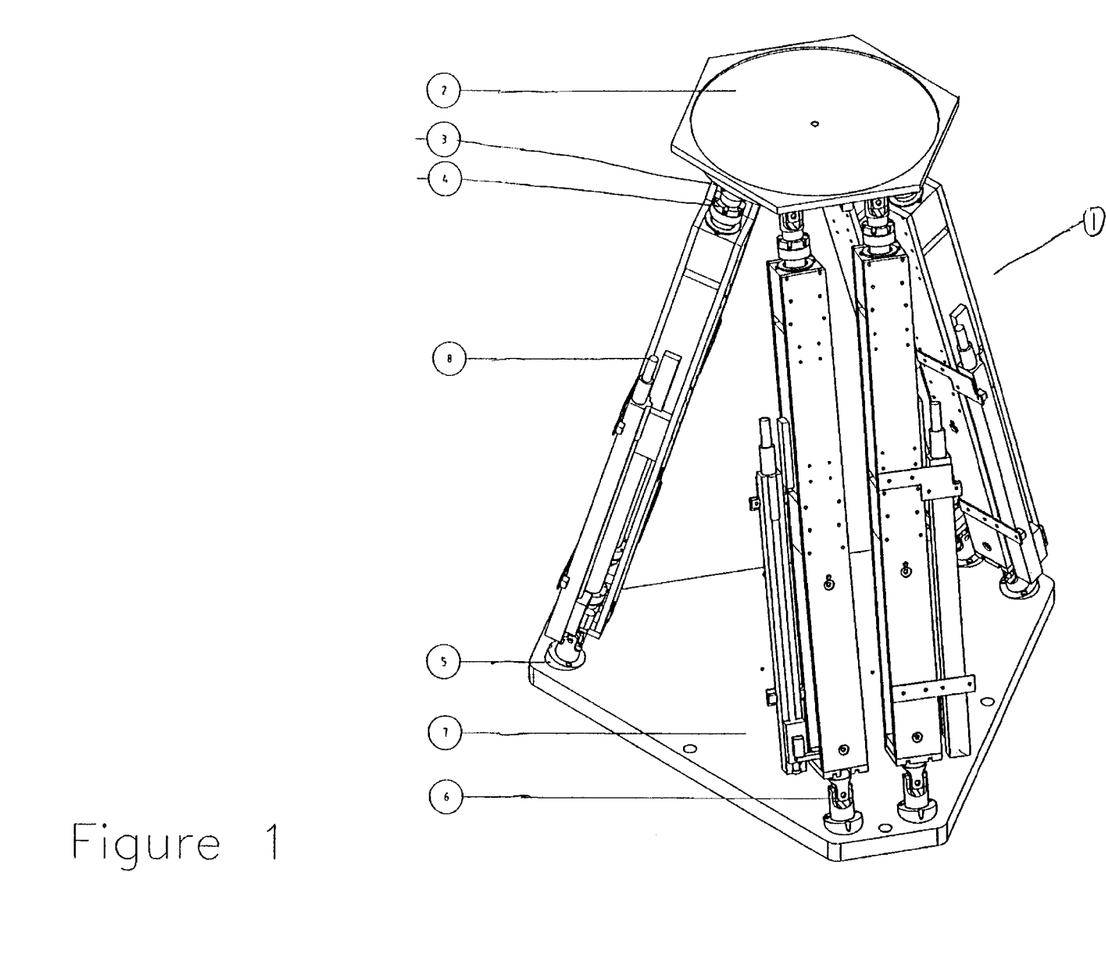
FIG. 1 is a perspective view of one embodiment of a motion platform of the present invention.

The apparatus (1) shown in the Figures comprises a base plate (7) which may be rigidly fastened to a massive object, such as the ground or floor of a building. It can be fastened to the walls or ceiling of a structure providing that these surfaces are strong enough to provide complete rigidity through the operating range of the motion platform. Mounting adapters (5) and actuator joints (6) connect linear actuators (8) to the base plate (7). The mounting arrangement is identical for each of the six linear actuators (8). The mounting adapter (5) is designed to maintain the orientation and location of the rotational centre of joint (6) in a precise pose with respect to the geometric centre of the base plate (7). In one embodiment, the design of mounting adapter (5) and its placement position on base plate (7) is governed by a set of relationships and methodologies that relate the machine configuration to the desired working volume and range of movement of the motion platform (1). These relationships and methodologies are detailed below.

Joint (6) must provide at least two independent axes of rotation and the axes of rotation must intersect such that there is a centre of rotation that does not move with respect to the base plate (7). In one embodiment, commercially available universal joints (Item Number UJ-NB435-1004 from Belden Inc. of Broadview, Ill.) were used for joint (6). Other commercially available or custom designed joints could be used providing they satisfy the principle requirement regarding a non-moving center of rotation and have strength, wear and friction characteristics that are compatible with the intended application.

Joints (4) and mounting adapters (3) connect the linear actuators (8) to the strike plate (2). The requirements for joints (4) and mounting adapters (3) are the same as the requirements for the joints (6) and the mounting adapters (5) on the base plate (7). In one embodiment, joints (4) and mounting adapters (3) on the strike plate (2) are identical to the base plate joints (6) and mounting adapters. However, the strike plate mounting adapters (3) and joints (4) need not be identical to their counterparts on the base plate (7) so long as they satisfy the configuration requirements for the motion platform (1) and are suitable for the intended application.

The placement position for mounting adapter (3) on strike plate (2) are governed by a set of relationships and methodologies that relate machine configuration to the desired working volume and range of movement of the motion platform (1). These are the same relationships and methodologies that determine the design of mounting adapters (3, 5) and determine the placement location of mounting adapter (3) on base plate (7) and are detailed below.

Strike plate (2) provides a surface on which the object to be moved can be mounted. Examples of such objects are cameras, communication antennas, people and articles to be tested through a motion sequence. In one embodiment, the strike plate (2) serves as a mounting surface for a carpet material, and is moved to strike a stationary shoe in a manner that replicates the kinematics of human running. For this application and others, it is preferable that the strike plate (2), mounting adapter (3) and joint (4) are all manufactured from aluminum to minimize the 'flying' weight of motion platform (1). These components can be made from materials other than aluminum depending on the needs of the intended application.

Figure 1A:
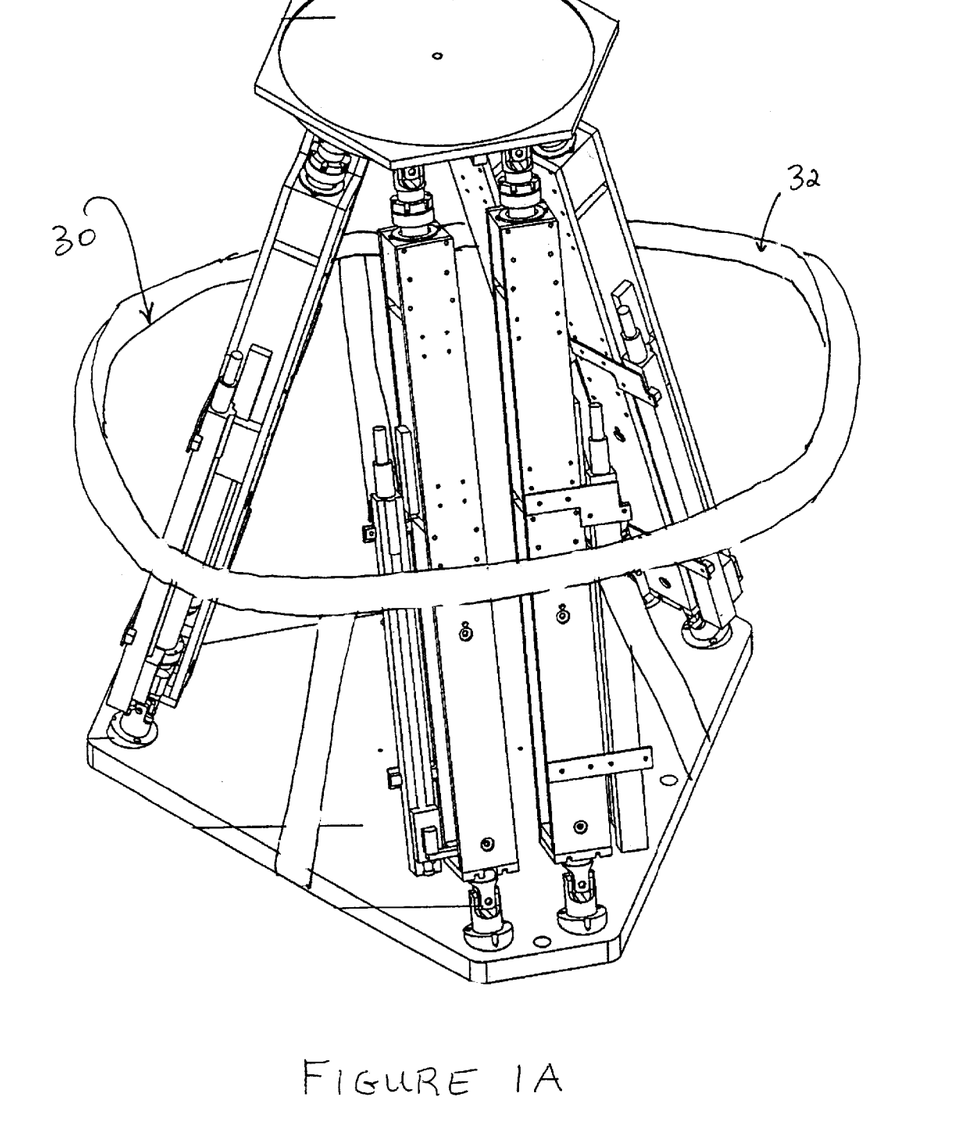
FIG. 1A is a perspective view of one embodiment illustrating the crash ring.

The motion platform may include an additional component referred to as a "crash ring" (30). The crash ring (30) is a passive component that encircles the motion platform at a distance that does not interfere with normal movement. It may be lined with a resilient cushioning material (32) to soften contact with the linear actuators (8). The crash ring (30) acts as a physical stop for the motion platform during situations where the device topples over to the side of its work envelope. This situation normally occurs when the motion platform loses power when it is displaced laterally from its center position. The crash ring prevents physical damage to the motion platform during these incidents and allows the motion platform to be quickly returned to its centered home position.

The operating characteristics for the linear actuator (8) are determined by a set of relationships and methodologies that relate machine performance to the position, velocity and acceleration characteristics of the trajectories to be followed by the motion platform (1). In one embodiment, the linear actuator (8) may be a linear electric jack. Other types of custom designed or commercially available electric, hydraulic or pneumatic actuators could be used providing that they permit movement only along one axis and that they satisfy the motion requirements for the intended application.

Figure 2:
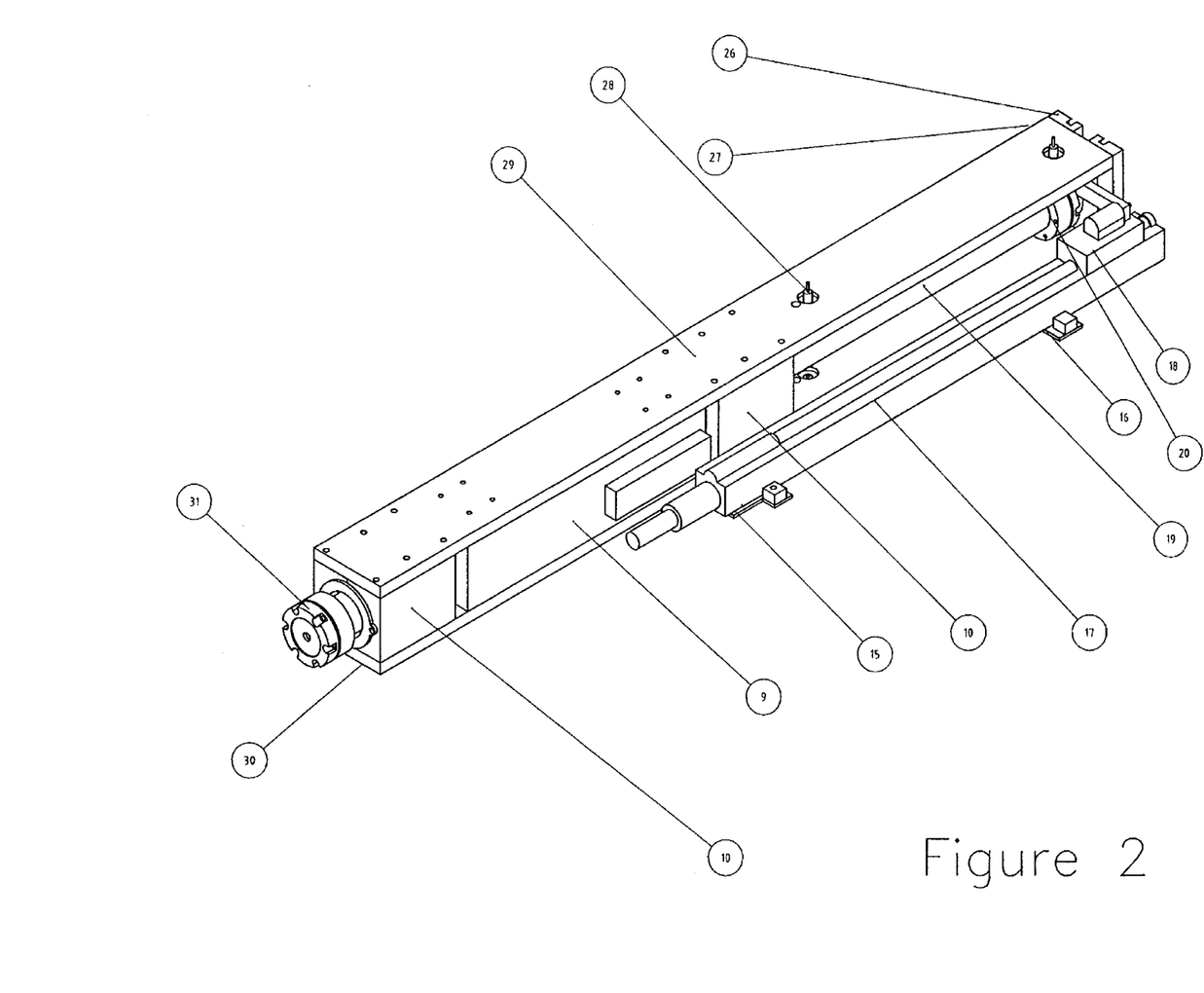
FIG. 2 is a view of one linear actuator of one embodiment.

Referring to FIG. 2, the linear motor assembly (8) is composed of a number of key sub-components: a linear electric motor block (9) and magnetic thrust rod (19); bearing assemblies (10); side rails (29, 30) and bottom plate (26); rod end clamps (31); encoder (17), encoder mounts (15 16); and encoder connecting rod (20).

The linear electric jack relies on a linear electric motor, composed of a powered linear thrust block and a thrust rod (19) which is a stainless steel tube packed with magnets. In one embodiment of the linear electric jack, the LD3808 linear electric motor block was used in conjunction with a 38 mm thrust tube, which are both commercially available from Linear Drives of Basildon, Essex, U.K.

The motor housing may be comprised of two supporting aluminum rails (29, 30) and an end plate (26). This open structure permits internal cooling within the motors and, with appropriate material selection, a strong load path that supports anticipated loads, the motor, bearing housings (10), linear measurement system (17), and any other external mounting requirements. The end plate (26) completes the structure and provides an additional coupling surface for externally mounted components. In one embodiment, gauge aluminum plate was used to make the rails (29,30) and end plate (26). If appropriately dimensioned for strength and cooling, other materials including plastic, steel or composites (such as fiberglass) could meet the requirements of this linear electric jack.

Figure 3:
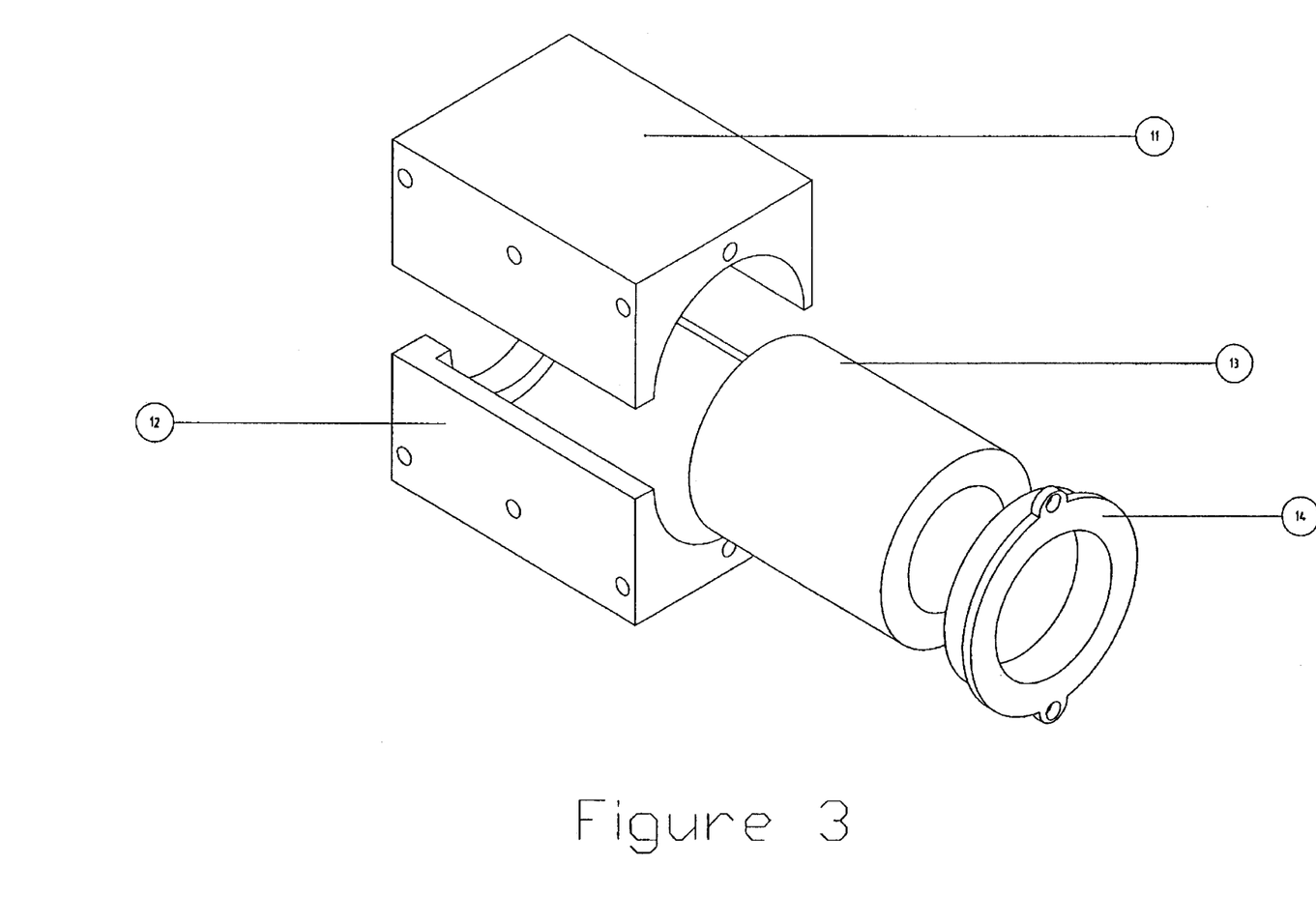
FIG. 3 is an exploded view of a bearing and bearing housing of one embodiment of a linear actuator.

The magnetic thrust rod (19) is driven linearly through the hollow motor block (9) when appropriately commutated current is applied to the motor. The rod (19) is held clear of the motor block's inner wall by two bearing assemblies (10) on either side of the thrust block. Referring to FIG. 3, the bearings (13) are held rigidly by bearing housings (11,12) and a bearing retaining ring (14). For linear electric motors, these bearings should preferably be dry (unlubricated) and made of a material with properties such as low back electromotive force (EMF) and low friction. Such materials may include carbon or plastic. The bearing housings should also be manufactured using material with low back EMF properties such as plastic or brass. Both the bearings (13) and the bearing housings (11, 12) may be split to facilitate in situ removal and/or replacement of bearing components without disassembly of the linear electric jack. In one embodiment of such split bearing assemblies, the bearings (13) were composed of a Carbon/Resin composite, a dry running low friction material, and custom manufactured by Advanced Carbon Products of Hayward, Calif., USA. In this same embodiment, the bearing housings were made from Ertalite™, a light, strong, plastic with no back EMF characteristics manufactured by DSM Engineering Plastic Products of Reading, Pa., USA.

Figure 4:
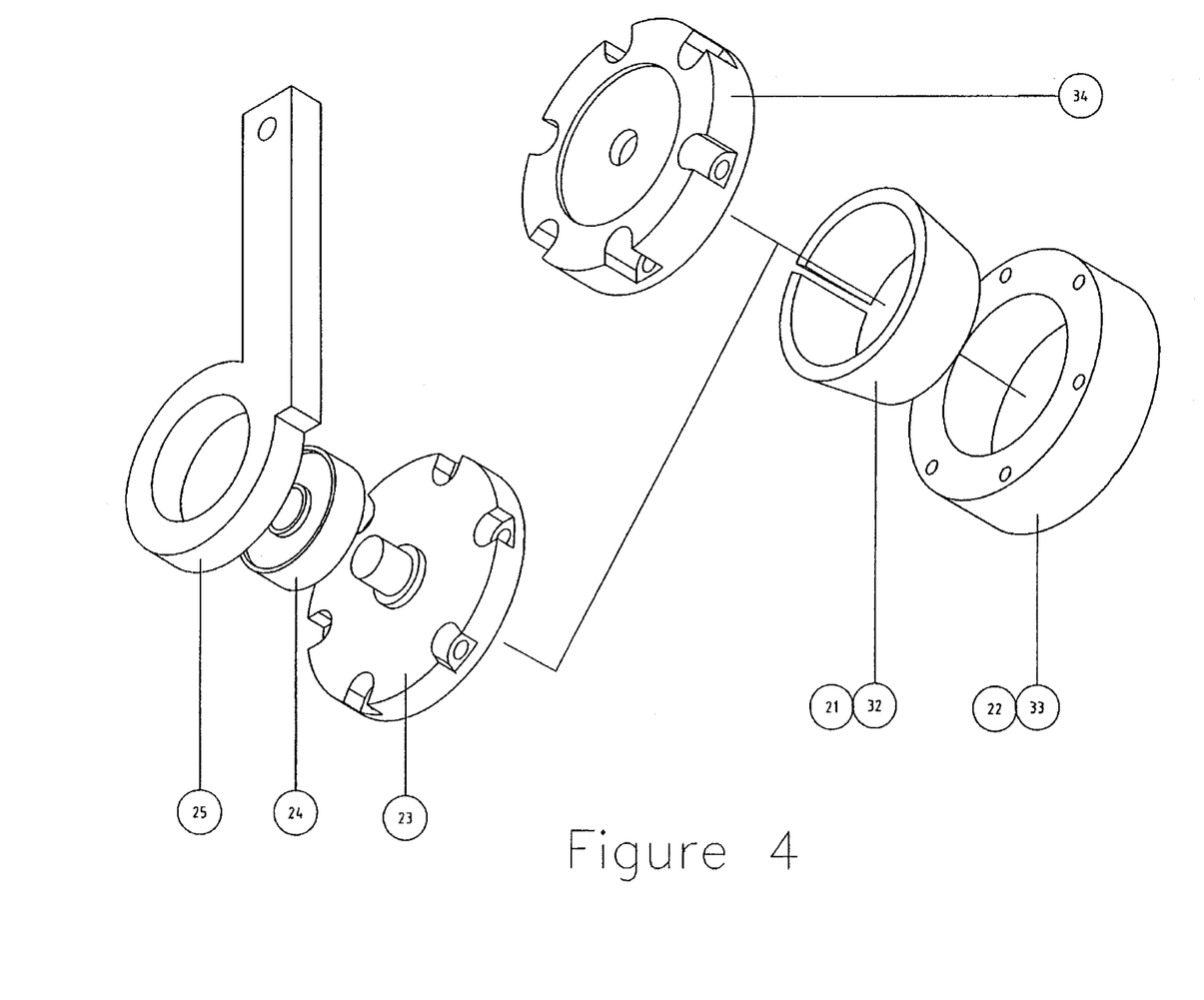
FIG. 4 is an exploded view of a rod end clamp.

Rod end clamps (20, 31) permit the attachment of payloads to the thrust rod (19) and, for the interior rod end clamp (20), prevents the thrust rod (19) from exiting the motor assembly. Referring to FIG. 4, the rod end clamps (31) are designed to provide solid attachment points to the rod without machining the rod surface or end components and to provide a solid impact surface during overstrokes. The clamps may comprise a split clamp ring (21), a clamp collar (22), and a clamp compression plate (34). The thrust rod (19) is inserted into the clamp collar (22) and clamp ring (21) such that the wedge profile of the ring fits snugly into the collar. The compression plate (34) is then fastened to the clamp collar using a number of appropriately sized industrial fasteners. As these fasteners are tightened, the clamp collar (22) and clamp ring (21) are pulled against the compression plate (34). The wedge profile of the clamp ring (21) and collar (22) drives the clamp ring (21) against the rod (19) surface. As the clamp ring (21) is compressed, the compression plate (34) is pulled against the rod (19) end. In this embodiment, the compression plate (34) provides both a firm payload mount and a reliable geometric reference relative to the rod end (19) which is important for precision motion. The angle of the wedge $\theta$ is related to clamping force, $N_b$, and the coefficient of static friction, $\mu_a$, through an explicit relationship expressed below:

$$N_s = \frac{F_b(\cos\theta - \mu_a \sin\theta)}{\sin\theta + \mu_a \cos\theta} \quad (1)$$

To provide closed loop control of the motor, the control system must receive the motor position as feedback. There are many encoders (15) which are commercially available and suitable for use with the present invention. Any linear measurement system of appropriate resolution could be used for this task, however many suffer from problems common to linear measurement systems requiring moving power and signal connections. These latter systems should preferably be avoided. In one embodiment, a magneto-strictive encoder was used. These devices are typically composed of a passively magnetic encoder carriage (18) and an encoder body (17), containing magnetically sensitive material through which the time-of-transit of an ultrasonic pulse is measured and converted into displacement by means of internal electronics. In one embodiment, the LP-38 ISI magneto-strictive encoder from TRelectronic GmbH of Trossingen, Germany was selected to provide A quad B incremental output to the system's control electronics. The control electronics in one embodiment of the present invention may be an IDC B8001 servodrive from Industrial Devices Corporation of Petaluma, Calif., and a Delta Tau PMAC1 by Delta Tau Data Systems of Northridge, Calif., USA.

The encoder carriage (18) limited to strictly linear motion can be connected to the interior rod end (19) through an encoder connector assembly (20). The encoder connector assembly is composed of a modified rod end compression plate (23) with a short shaft, a bearing (24), and a connector rod (25). The connector rod (25), bearing (24) and compression plate shaft (23) are joined by press fitting, for example, into a single assembly that permits free rotation of the connector rod about the shaft of the compression plate (23). Therefore, the encoder connector assembly permits the thrust rod (19) to rotate freely about the rod axis without applying detrimental forces to the encoder while communicating rod linear motion rigidly to the linear encoder (17). Encoder mounting plates (15, 16) provide an offset distance for the linear encoder, typically dependent on the encoder type and EM sensitivity properties of the encoder. Other linear measurement systems such as LVDTs, laser interferometers, and glass scale encoders might also be applied to this system and, depending on the placement and measurement principle, might or might not require specific rod end couplers.

Unlike some rotary motors, linear motors are capable of exceeding mechanical limits and damaging components in the process, an event called "overstroke". To prevent this possibility, the actuator (8) may use positive and negative limit switches (28) that disable the motor when triggered by the entry of the rod into a dangerous region. In one embodiment, Banner D12 optical switches by Banner Engineering Corporation of Minneapolis, Minn., monitor and enforce the linear actuators interior geometric limits and disable the amplifiers on overstroke. Such switches (28) may be further used to implement homing triggers for precise calibration of the motor position.

The damage from an overstroke event may further reduced through the selection of appropriate end plate bumper (27) and rod end ring bumpers. In one example, the rod end ring bumper may be manufactured of neoprene while the lower bumper may be made of 40 duro gum rubber. The rod end ring bumper can be fixed either to the bearing housing (10) or rod end clamp collar (22) as convenient.

Figures 5, 5A:
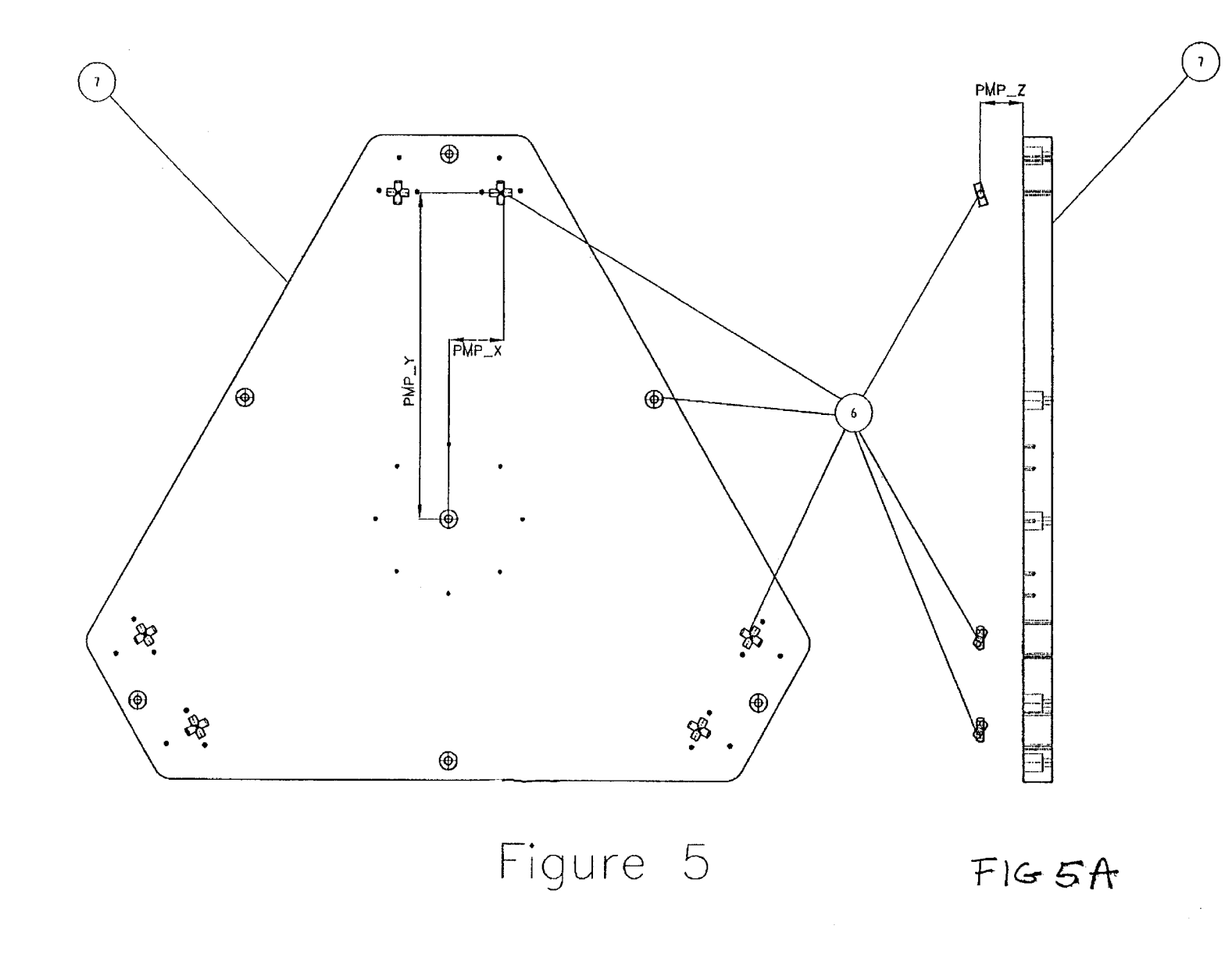
FIG. 5 is a top plan view of the base plate.
FIG. 5A is a side view of the base plate.
Figure 6:
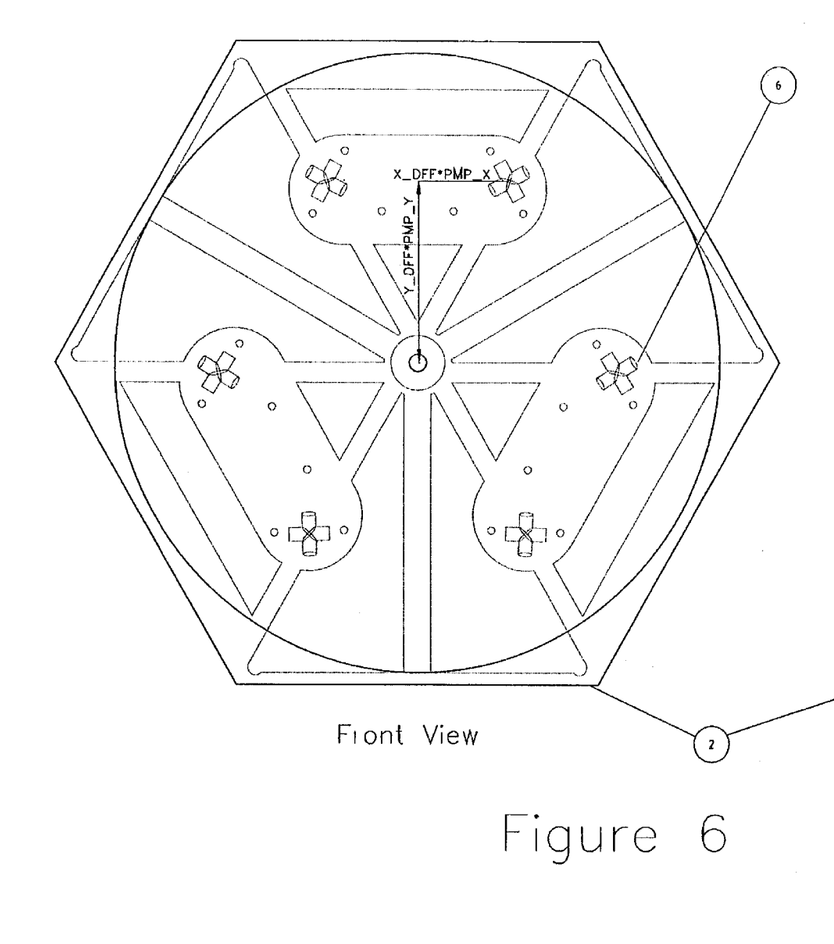
FIG. 6 is a bottom view of the strike plate.
Figure 6A:
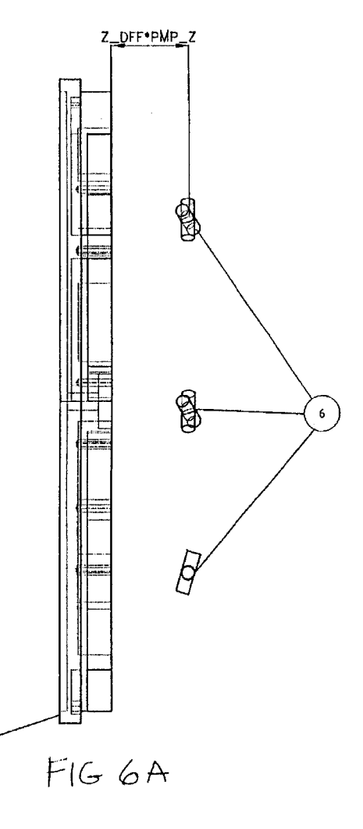
FIG. 6A is a side view of the strike plate.

The relationships and methodologies that relate machine configuration to the desired working volume and range of motion of the motion platform (1) are now described. The location of the center of rotation of joint (6) on base plate (7) is governed by three independent parameters that are measured from the geometric center of base plate (7) as illustrated in FIG. 5:

PMP_X—Primary Mounting Point X value
PMP_Y—Primary Mounting Point Y value
PMP_Z—Primary Mounting Point Z value The location of the center of rotation of joint (4) on strike plate (2) is governed by three independent scaling factors that are applied respectively to PMP_X, PMP_Y and PMP_Z as illustrated in FIG. 6:

X_DFF—X Dimension Form Factor
Y_DFF—Y Dimension Form Factor
Z_DFF—Z Dimension Form Factor The location of the center of rotation of joint (4) on strike plate (2) is measured from the geometric center of strike plate (2). The geometric center of strike plate (2) is itself centered on the geometric center of base plate (7) with an offset in the Z (vertical) direction.

Figures 7, 7A:
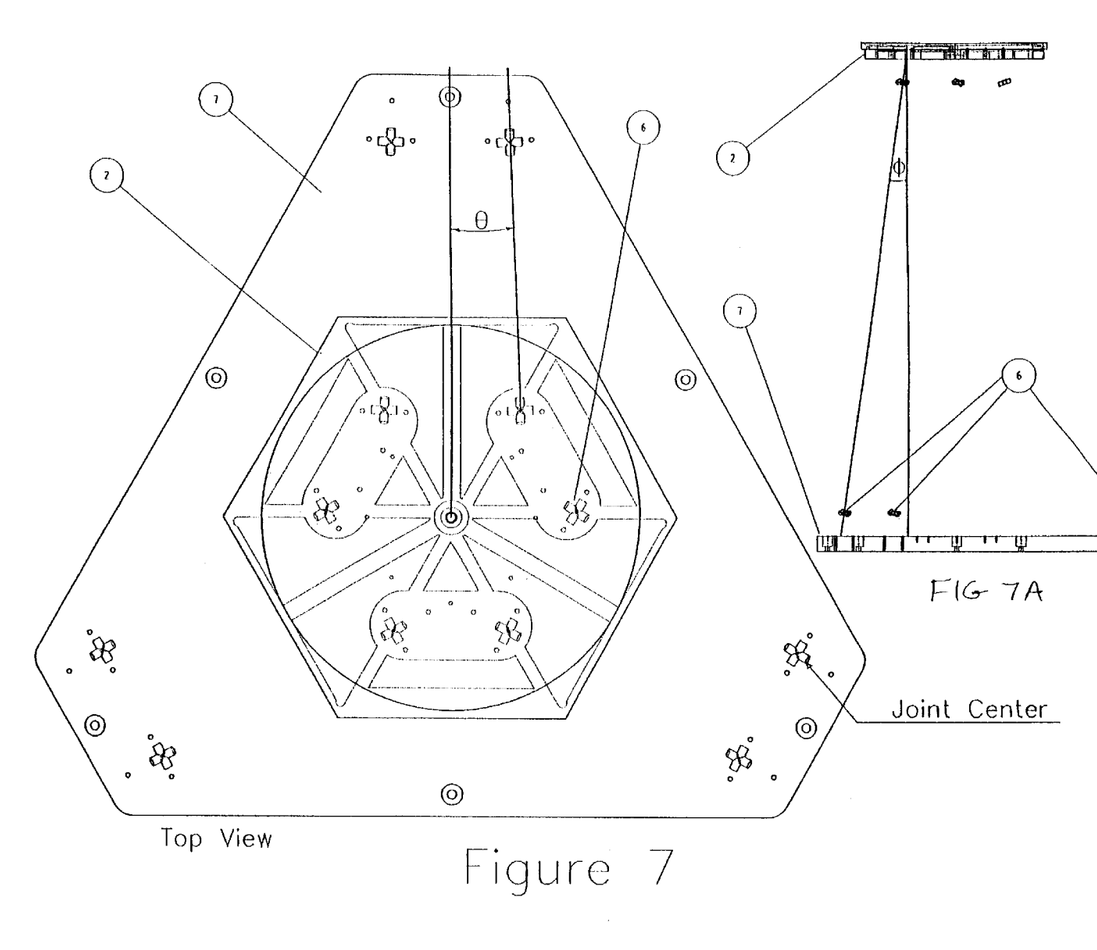
FIG. 7 is a top view of the strike plate superimposed over the base plate.
FIG. 7A is a schematic side view of the strike plate and base plate.

The length of linear actuator (8) determines the linear distance between the center of rotation of joint (6) on base plate (7) and the center of rotation of joint (4) on strike plate (2). Once the value for the length of the linear actuator is established and values are set for PMP__X, PMP__Y, PMP__Z, X__DFF, Y__DFF and Z__DFF the configuration of motion platform (1) is calculated and its corresponding range of motion and working volume is established. The azimuth (θ) and altitude (φ) angles (see FIG. 7) of mounting adapters (3, 5) are calculated using the following relationships:

$$\theta = ATAN2[((PMP\_X/2-\sqrt{3}*PMP\_Y/2)+X\_DFF*PMP\_X),(Y\_DFF*PMP\_Y-(\sqrt{3}*PMP\_X/2+PMP\_Y/2))] \quad (2)$$

$$\phi = ACOS[L/S] \quad (3)$$

where:
S=the neutral or homed length of linear actuator (8); and
$L=(S^2-((PMP\_X/2-\sqrt{3}*PMP\_Y/2)+X\_DFF*PMP\_X)^2 -(Y\_DFF*PMP\_Y-(\sqrt{3}*PMP\_X/2+PMP\_Y/2))^2)^{1/2}$ This design insures that linear actuator (8) and its corresponding joints are held inline when the linear actuator (8) is in its "homed" or neutral position (as defined by the length value for the Linear Actuator used in the above calculations). By maintaining this 'inline' configuration the maximum working volume for motion platform (1) is realized with a given joints (4, 6).

Having a desired trajectory for strike plate (2) allows the calculation of the corresponding movements that each of the six linear actuators (8) must make in order to achieve this motion. The desired trajectory is represented mathematically by a matrix of 4×4 transforms that represent the position and orientation (i.e. the 'pose') of strike plate (7) through the duration of the trajectory. Each element of the trajectory matrix is a 4×4 transform that represents the pose of strike plate (7) at a moment in time. The first element of the trajectory matrix is the pose of strike plate (7) at the beginning of the trajectory. Each subsequent element of the trajectory matrix represents the pose of strike plate (7) at a specific interval of time after the beginning of the trajectory. The last element of the trajectory matrix represents the pose of strike plate (7) at the end of the trajectory. The positions of the centers of rotation of each of the joints (4) can be calculated using the following formula:

$$\vec{p}_{t=i} = T_{t=i} \vec{p}_{t=0} \quad (4)$$

Where: p=a 6×4 array representing the positions of the centers of rotation of joints (4) in Cartesian coordinates
T=the trajectory matrix
t=time
i=a time interval with the trajectory matrix
't=0' represents the beginning of the trajectory The length of each of the linear actutators (8) at each time interval along trajectory can then be calculated by subtracting the position of the center of rotation of joint (6) from the position of the center of rotation of joint (4) attached to the linear actuators (8). The formula for this calculation is:

$$l_{n \text{ at } t=i} = \sqrt{(\vec{P}_{n \text{ at } t=i} - \vec{B}_n)(\vec{P}_{n \text{ at } t=i} - \vec{B}_n)} \quad (5)$$

Where:
$l_{n \text{ at } t=i}$—is the length of 'n'th linear actuator (8), at the 'i'th time interval along the trajectory and 'n' ranges from 1 to 6 for each of the six linear actuators (8)
P—is the position of the center of rotation of joint (4) in Cartesian coordinates on the 'n'th linear actuator (8) at the 'i'th time interval B—is the position of the center of rotation of joint (6) in Cartesian coordinates on the 'n'th linear actuator (8) at the 'i'th time interval Having established the movements for each of the linear actuators (8) it can then be determined if the joints (4, 6) can accommodate this motion. A mathematical model of the motion platform is used to determine the corresponding motions of joints (4, 6). In one embodiment of the current invention a software package called "Working Model" (The MacNeal-Schwendler Corp. of San Mateo, Calif.) was used to build the mathematical model of motion platform (1) and carry out the analysis. Other means of numerical analysis could be used to gain the same result. Depending on the outcome of the analysis on the movements of joints (4, 6) the parameters PMP__X. PMP__Y, PMP__Z, X__DFF, Y__DFF and Z__DFF, as well as the length of linear actuator (8), can be adjusted until an appropriate configuration is found to suit the desired trajectory(s).

The configuration of motion platform (1) may be readily adapted by those skilled in the art to a wide variety of other applications, such as multi-degree of freedom material testing. In one embodiment of the invention, a specific example is the testing of shoes to determine the effect shoe design has on motion of the human ankle. In this application, a test shoe is held stationary by appropriate fixturing while the motion platform becomes the 'ground'. A movement path, or trajectory, is determined for the motion platform that creates the same relative motion between foot and ground as is experienced in normal human running or walking movement. Instrumentation mounted either to the ground or to the fixturing holding the test shoe measures the response of the shoe specimen to the application of the trajectory. These measurements can then be interpreted to reveal the desired information regarding the projected impact of the specimen on human movement.

Figure 8:
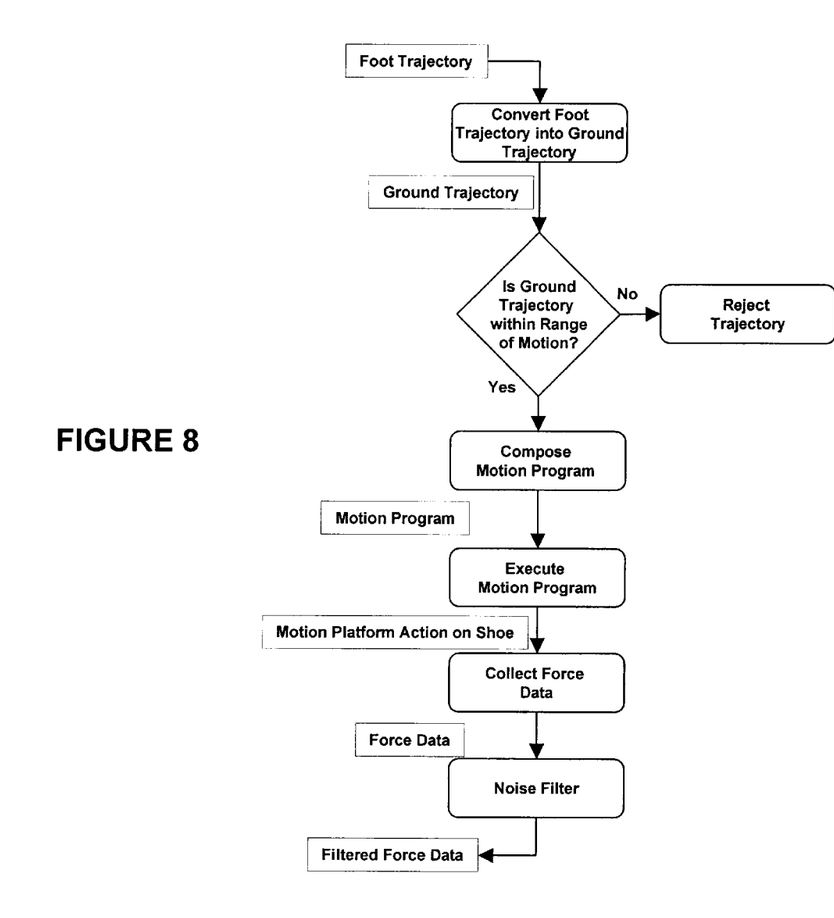
FIG. 8 is a schematic flowchart of one embodiment of a method of the present invention.

A schematic flowchart of one method of the present invention is shown in FIG. 8. During a typical athletic movement, the motion of a human foot with respect to a fixed point on the ground and expressed over time is known as a foot trajectory. This trajectory can be either measured from human subjects or generated through computer simulation. A foot trajectory may be transformed into a trajectory of the ground relative to the foot using computer software following the calculations outlined herein. Additional "inverse kinematics" software can transform this trajectory into a set of six linear actuator trajectories for a motion platform. These trajectories can then be formatted into instructions for an appropriate off-the-shelf or customized motion platform controller. Once executed, these instructions can move the strike plate into the footwear specimen. A six degree of freedom force sensor in the "ankle" (or other location) of the specimen can then be used for force data capture. Together this process enables the discovery of forces experienced by the foot given a specific foot trajectory and shoe specimen.

Because the foot translates and rotates about all three Cartesian axes, a foot trajectory is a six degree of freedom trajectory. To describe a "pose" at a particular time in this trajectory requires a position vector and some expression of orientation (e.g. orientation matrices, quaternions, euler angles, etc.). The trajectory is, therefore, an ordered set of such "poses" over time. The pose of a point on the foot with respect to some Cartesian coordinate system fixed to the ground can be represented mathematically by a 4×4 matrix that incorporates both position and orientation information. The 4×4 matrix is referred to as a 'transform' and is symbolically represented as:

$$^{GCS}_{FCS}T \quad (6)$$

where:
T—is a 4×4 numeric matrix
GGS—is the reference Ground Coordinate System
FCS—is a point attached rigidly to the foot and the Foot Coordinate System
A foot trajectory over time can therefore be represented as:

$$^{GCS}_{FCS}T_i \quad (7)$$

where—i represents the $i^{th}$ time interval (0, 1, 2, . . . )

The foot trajectory can be measured from human subjects using machine vision techniques (e.g. Motion Analysis Corporation of 3617 Westwind Blvd., Santa Rosa, Calif. 95403). The cartesian position of reflective targets, applied to a human subject, are measured using software that processes images from a system of high speed digital cameras. The positions of these targets are then used to establish the kinematics of motion for the subject. Application of targets to known locations on the human foot therefore permits the measurement of the foot trajectory.

Foot motion can be simulated through the use of dynamic analysis software such as LMS DADS from LMS INTERNATIONAL, Researchpark Z1, Interleuvenlaan 68,3001 Leuven, Belgium. Given the dimensions, mass and inertia of the human skeleton and muscle tissue, methods of human gait generation can be explored and an appropriate foot trajectory produced.

The foot trajectory may then be used to calculate a motion platform trajectory. The motion platform trajectory matrix, represented as T in the prior discussion of the motion platform design, can be calculated by the following formula:

$$T_i = {}^{BCS}_{FCS}T \cdot ({}^{GCS}_{FCS}T_i)^{-1} \cdot {}^{GCS}_{PCS}T \quad (8)$$

where:
BCS—is the Base Coordinate System for the motion platform;
PCS—is the strike Plate Coordinate System, which is rigidly attached to the strike plate; and
i—represents the $i^{th}$ time interval (0, 1, 2, . . . )
The transform $$^{BCS}_{FCS}T$$

describes the pose of the Foot Coordinate System (FCS) within the Base Coordinate System framework. Since the pose of the FCS within the BCS is stationary for any given movement of the motion platform this transform can be deduced from the geometry of the motion platform, the fixturing holding the test shoe and the placement of these two items with respect to each other.

The Ground Coordinate System (GCS) framework is attached rigidly to the strike Plate Coordinate System (PCS) since the strike plate is acting as the 'ground' in this application. The transform $$^{GCS}_{PCS}T$$

describes the pose of the PCS within the GCS framework. This transform is not time dependent and can be deduced from the geometry of the strike plate and parameters established by the user.

The transform $$^{GCS}_{FCS}T$$

that represents the pose of the foot in the GCS must be inverted for this calculation using ordinary methods for inverting matrices. A 4×4 matrix that is structured correctly to represent pose data is normally invertable.

Figure 9:
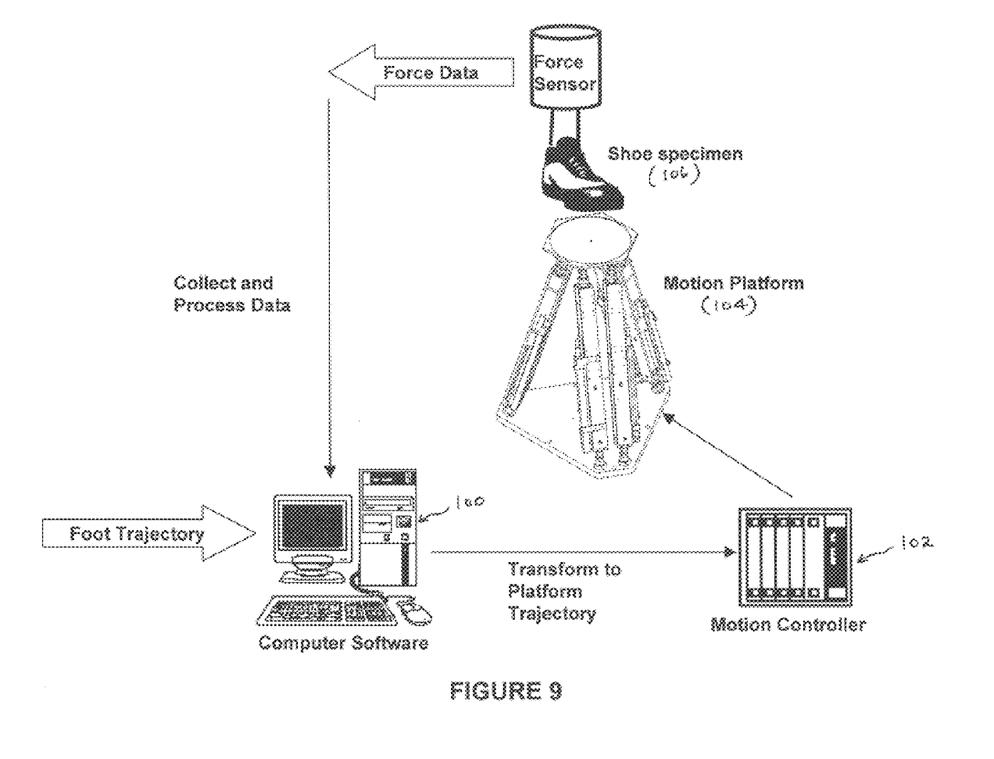
FIG. 9 is a schematic representation of one embodiment of a footwear test apparatus of the present invention.

As shown in FIG. 9, one embodiment of the footwear test apparatus is configured to discover ankle force data from a foot trajectory within the motion platform system. The apparatus may comprise a computer (100) or other processing means, a motion controller (102), the motion platform (104), and an instrumented foot specimen (106). The computer (100) may be used both to execute the transformation and inverse kinematics routines and to collect and process the resulting force data.

Since the motion platform mimics the ground striking the foot, a computer must execute software that manipulates and transforms the foot relative to ground trajectory into an appropriate ground relative to foot trajectory following the calculations outlined above. This software can be further used to shift and/or rotate this trajectory into a position and/or orientation that best exploits the motion platform's range of motion. These translations or rotations must, of course, be reflected in the positioning of the foot specimen in the motion platform's coordinate system. Inverse kinematics routines within the computer software can then be used to convert this desired ground trajectory into a set of six leg trajectories for the motion platform. These leg trajectories can then be formatted into appropriate motion commands and uploaded to the platform's motion controller.

Any industrial motion controller capable of regulating and coordinating the position of six axes can execute the motion program using either standard PID (Proportional-Integral-Derivative) or custom (e.g. adaptive) control algorithms. The motion controller issues instruction to the motors' drives in turn, producing motion in each motor axis.

Figure 10:
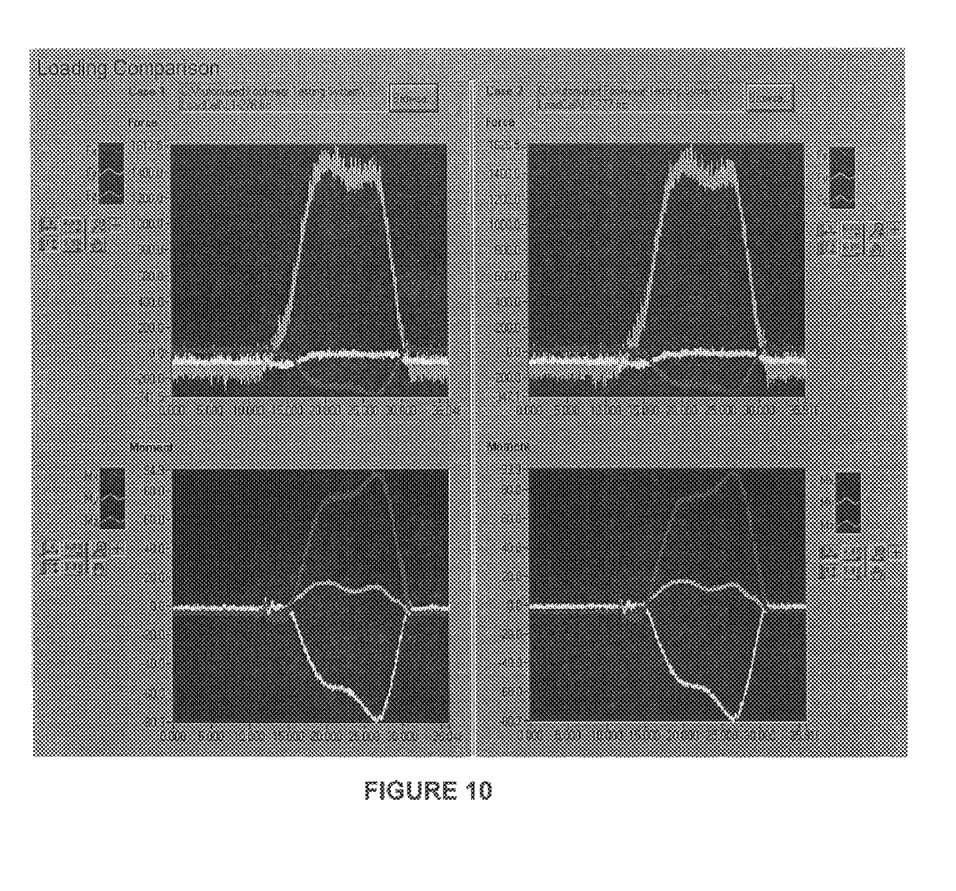
FIG. 10 is a screen shot of exemplary output graphs from a footwear test of the present invention.

If the motion platform trajectory has been appropriately planned, the strike plate of the platform will contact the shoe specimen. If the shoe has been instrumented with a six degree of freedom force sensor, the forces of contact at the shoe can be transformed into forces in the ankle and returned for further processing as required. A screen shot of temporally distributed forces measured using an apparatus and method of the present invention is shown in FIG. 10.

As will be apparent to those skilled in the art, various modifications, adaptations and variations of the foregoing specific disclosure can be made without departing from the scope of the invention claimed herein.

What is claimed is:

1. A shoe testing apparatus comprising:
   (a) a fixed artificial foot for wearing the shoe, wherein the artificial foot is mounted to a force sensor;
   (b) a motion platform having 6 degrees of freedom of movement;
   (c) means for actuating the motion platform and striking the shoe with the platform in a manner simulating the running or walking gait of a shoe wearer; and (d) means for recording the forces transmitted through the shoe to the artificial foot and sensed by the force sensor.

2. The apparatus of claim 1 wherein said motion platform comprises a base, a platform, a motion controller and at least 6 linear actuating mechanisms disposed between and connected to the base and the platform, wherein each actuating mechanism comprises an electromagnetic linear actuator comprising an electric thrust block and a magnetic thrust rod and each actuating mechanism is controlled by the motion controller.

3. The apparatus of claim 1 wherein said means for actuating the motion platform comprises:

(a) means for transforming a foot trajectory to a ground trajectory; and (b) means for causing the motion platform to execute the ground trajectory.

4. The apparatus of claim 2 further comprising a support ring encircling the actuating mechanisms.

5. The apparatus of claim 4 wherein said support ring comprises an inner resilient cushioning material.

6. The apparatus of claim 2 wherein each said electromagnetic linear actuator further comprises a positional encoder operatively connected to the motion controller.

7. The apparatus of claim 6 wherein each said positional encoder comprises a magneto-strictive encoder.

8. The apparatus of claim 2, wherein each said electromagnetic linear actuator further comprises a cylindrical bearing comprising a low back EMP or non-metallic material.

9. The apparatus of claim 8 wherein each said low back EMF or non-metallic material includes a plastic or a carbon-resin composite material.

10. A method of testing a shoe comprising the steps of:

(a) fitting an artificial foot within the shoe, providing a force sensor attached to the artificial foot and fixing the foot and shoe in position;

(b) providing a motion platform having 6 degrees of freedom of movement;

(c) providing a foot trajectory and transforming the foot trajectory to a platform trajectory;

(d) actuating the motion platform with the platform trajectory to strike the shoe; and (e) recording the force transmitted through the shoe to the artificial foot with the force sensor.

11. The method of claim 10 wherein the force sensor records forces in 6 degrees of freedom.

12. The method of claim 10 wherein said motion platform comprises a base, a platform, a motion controller and at least 6 linear actuating mechanisms disposed between and connected to the base and the platform, wherein each actuating mechanism comprises an electromagnetic linear actuator comprising an electric thrust block and a magnetic thrust rod and each actuating mechanism is controlled by the motion controller.

* * * * *